United States Patent [19]

Pedrazzoli et al.

[11] 4,282,247
[45] Aug. 4, 1981

[54] 5-(2-HYDROXY-3-THIOPROPOXY) CHROMONE-2-CARBOXYLIC ACIDS CHEMICAL PROCESS AND PHARMACEUTICAL COMPOSITIONS

[75] Inventors: Andrea Pedrazzoli, Milan; Sergio Boveri, Monza, both of Italy

[73] Assignee: CM Industries, Paris, France

[21] Appl. No.: 134,690

[22] Filed: Mar. 27, 1980

[30] Foreign Application Priority Data

Apr. 6, 1979 [FR] France .............................. 79 08859

[51] Int. Cl.$^3$ ..................... A61K 31/35; C07D 311/22
[52] U.S. Cl. ................................. 424/283; 260/345.2
[58] Field of Search ...................... 260/345.2; 424/283

[56] References Cited

U.S. PATENT DOCUMENTS

| 3,427,324 | 2/1969 | Fitzmaurice | 260/345.2 |
| 3,484,445 | 12/1969 | Lee et al. | 260/345.2 |
| 3,786,071 | 1/1974 | Cairns et al. | 260/345.2 |

FOREIGN PATENT DOCUMENTS

| 1604165 | 9/1971 | France | 260/345.2 |
| 1093673 | 12/1967 | United Kingdom | 260/345.2 |
| 1223690 | 3/1971 | United Kingdom | 260/345.2 |

*Primary Examiner*—Nicky Chan
*Attorney, Agent, or Firm*—Weingarten, Maxham & Schurgin

[57] ABSTRACT

Anti-anaphylactic and anti-allergic 5-(2-hydroxy-3-thiopropoxy) chromone-2-carboxylic acids of the general formula

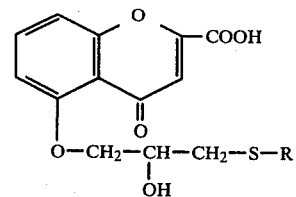

wherein R is alkyl, alkenyl, hydroxyalkyl, cycloalkyl, cyclo-alkylalkyl, their alkali and alkaline-earth metal salts and 1–4 C alkyl esters as well as a process for the preparation thereof and pharmaceutical compositions containing them.

4 Claims, No Drawings

5-(2-HYDROXY-3-THIOPROPOXY) CHROMONE-2-CARBOXYLIC ACIDS CHEMICAL PROCESS AND PHARMACEUTICAL COMPOSITIONS

The present invention relates to novel 5-(2-hydroxy-3-thiopropoxy)chromone-2-carboxylic acids having anti-anaphylactic and anti-allergic properties, to a process for their preparation and to pharmaceutical compositions containing them.

More particularly, the present invention relates to 5-(2-hydroxy-3-thiopropoxy)-chromone-2-carboxylic acids characterized by the following general formula

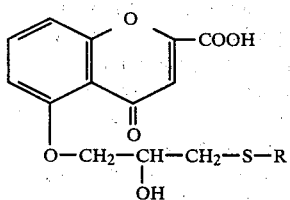

I in which R represents an alkyl group containing from 1 to 16 carbon atoms, an alkenyl group containing from 3 to 4 carbon atoms, a cycloalkyl group containing from 3 to 8 carbon atoms or a cycloalkyl-alkyl group containing from 4 to 9 carbon atoms, as well as to their alkali and alkaline-earth metal salts and their alkyl esters containing from 1 to 4 carbon atoms.

The British Pat. No. 1,093,673 describes a series of 5-alkoxychromone-2-carboxylic acids, differently substituted in the alkoxy group, characterized by the following general formula:

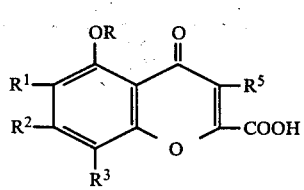

II and salts, esters and amides thereof in which $R^1$, $R^2$, $R^3$ and $R^5$ represent hydrogen or other substituents and R represents an alkyl group substituted by one or more free or esterified hydroxy groups or by a carboxyl group; an alkyl group or an aralkyl group interrupted by one or more oxygen atoms optionally substituted by one or more free or esterified hydroxy groups; an O-heterocyclic ring optionally substituted by one or more alkyl groups or by one or more, free or esterified hydroxy groups; or an alkyl group substituted by an O-heterocyclic ring optionally substituted by one or more alkyl groups. Said patent is not concerned with any chromone bearing at the 5 position an alkoxy group substituted by a thio group.

The French Pat. No. 1,604,165 describes a series of alkoxychromone-2-carboxylic acids, differently substituted in the alkoxy group, characterized by the following general formula

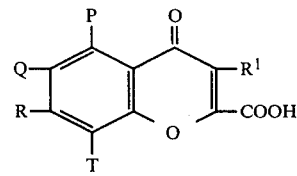

III in which P is hydrogen or a group other than OY and Q, R, T represent a hydrogen atom or a substituent other than hydrogen, one of the substituents Q, R and T being a group OY in which Y is an alkyl group substituted by one or more hydroxy or carboxy groups; an alkyl or aralkyl group in which one or more methylene groups are replaced by an oxygen or sulfur atom or by a carbonyl group and may be substituted by one or more hydroxy or carboxy groups; a heterocyclic group containing carbon and oxygen atoms, optionally substituted by one or more hydroxy or alkyl groups; or an alkyl group substituted by one or more heterocyclic groups. Although the formula III above includes in a general way chromones substituted in the benzene ring by an alkoxy group substituted by a grouping thio, said grouping is never in the 5 position. Moreover, no chromone substituted in the benzene ring by a thio alkoxy group is disclosed in the specification of the above mentioned patent.

It has now been found that the 5-(2-hydroxy-3-thiopropoxy) chromone-2-carboxylic acids of formula I above, their salts and $C_1$-$C_4$ alkyl esters, possess an anti-anaphylactic activity even superior to that of the corresponding products described in the British Pat. No. 1,093,673 having in the molecule an oxygen atom instead of a sulfur atom and to that of the corresponding products included in the general formula of the French Pat. No. 1,604,165 having the thio-alkoxy grouping in a position other than the 5 position of the chromone ring.

The 5-(2-hydroxy-3-thiopropoxy)chromone-2-carboxylic acids, the alkaline metal salts and esters thereof are prepared by treating a lower alkyl oxalate of formula (COOR°)$_2$, where R° is an alkyl group containing from 1 to 4 carbon atoms, with a 6-(2-hydroxy-3-thiopropoxy)-2-hydroxyacetophenone of formula

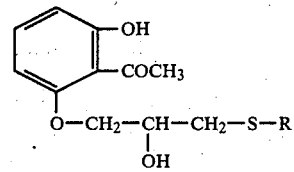

IV where R has the meaning defined above.

The reaction is carried out in the presence of a condensing alkaline agent, such as an alkali metal salt or an alkali hydride, amide or alcoholate, for example sodium methoxide or ethoxide, sodamide or metallic sodium in an inert organic solvent, such as dioxane, methanol, ethanol, benzene or mixtures thereof at the reflux temperature of the solvent employed.

According to a preferred embodiment, the condensation is carried out in benzene and in the presence of the alcohol R°OH and of the alcoholate R°ONa corresponding to the oxalate employed.

The reacting mixture is then acidified, preferably with hydrochloric acid, and heated at reflux for 10 to 30 minutes. Thus a cyclisation is performed with elimination of one mole of the alcohol R°OH and formation of a compound of formula

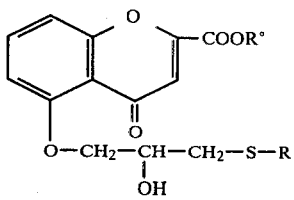

wherein R and R° have the meaning defined above. The product thus obtained is isolated from the reaction mixture following conventional techniques.

The lower alkyl 5-(2-hydroxy-3-thiopropoxy)chromone-2-carboxylates of formula V thus obtained can be then converted into the corresponding free acids (formula I) by hydrolysis in alkaline medium, for example by heating at reflux for 10 to 30 minutes in ethanol or methanol, in the presence of sodium or potassium hydroxide. At the end of the reaction the corresponding sodium or potassium salt or, by further acidification, the free acid can be isolated.

The preparation of the free acids is preferably carried out by reacting the 6-(2-hydroxy-3-thiopropoxy)-2-hydroxy-acetophenones of formula IV with methyl or ethyl oxalate. In such a manner, the cyclisation is favoured by the elimination of a mole of a low-boiling alcohol thus affording the ester V (R°=CH$_3$,C$_2$H$_5$) better yields in the step preceeding the hydrolysis reaction.

The products of formula I, in the form of free acids, can be converted into their non-toxic pharmaceutically acceptable salts following conventional methods, for example by reacting stoichiometric amounts of the alkali or alkaline-earth hydroxide with the free acid in aqueous solution. They are isolated by evaporation and crystallisation.

The 6-(2-hydroxy-3-thiopropoxy)-2-hydroxyacetophenones of formula IV used as starting compounds for the preparation of the 5-(2-hydroxy-3-thiopropoxy)chromone-2-carboxylic acids of the present invention are new products which can be prepared by reacting the (3-chloro-2-hydroxypropoxy)-2-hydroxyacetophenone with an excess of the alkali metal salt of the mercaptan RSH in benzene or toluene at a temperature of from 90° to 120° C. and by isolating them by conventional methods.

The 5-(2-hydroxy-3-thiopropoxy)chromone-2-carboxylic acids of the present invention, as well as their salts and their esters, inhibit the release and/or the action of toxic products or spasmogens arising from antigen-antibody reactions, as it has been shown in the tests of the anti-anaphylactic activity.

The 5-(2-hydroxy-3-thiopropoxy)chromone-2-carboxylic acids, their salts and their esters have been tested in rats by oral route to evaluate their ability to inhibit passive cutaneous anaphylaxis in animals sensitized to egg albumin and *Bordetella pertussis*.

As reference compounds there has been used:
product A: 7-(2-hydroxyethoxy)-9-oxoxanthene-2-carboxylic acid described in Brit.Med.J. 2, 93–95; 1974;
product B: 5-acetylsalicylic acid described in German Pat. No. 2,542,225;
product C: ethyl 5-(2-hydroxy-3-methoxypropoxy)-chromone-2-carboxylate, described in British Pat. No. 1,093,673;
product D: 7-(2-hydroxy-3-methylthiopropoxy)chromone-2-carboxylic acid; new product included in the general formula of the French Pat. No. 1,604,165, but not specifically described, which has been prepared as follows:

A mixture of 4.7 g of ethyl 7-hydroxychromone-2-carboxylate and 20 ml of 1-chloro-2,3-epoxypropane is heated at an external temperature of 100° C. for 8 hours in the presence of 0.2 ml of piperidine. The mixture is evaporated under reduced pressure and the residue is taken up with 15 ml of ethyl acetate. After filtration, the solution is evaporated under reduced pressure, the residue is taken up with 30 ml of chloroform and 10 ml of N hydrochloric acid, concentrated and stirred for one hour. The organic layer is washed with water, dried on anhydrous sodium sulfate and evaporated. The residue, crystallized from ethanol, gives 4 g of ethyl 7-(3-chloro-2-hydroxypropoxy)chromone-2-carboxylate. An amount of 1.65 g of the product thus obtained is dissolved in 40 mg of methylene chloride and to the solution thus obtained there is added 0.2 g of hexadecyltributylphosphonium bromide. To the organic solution there is added a solution of CH$_3$SNa in 20 ml of water. The mixture is stirred for two hours at the room temperature, the aqueous layer is separated and acidified with N hydrochloric acid. The precipitate which forms, consisting of 7-(2-hydroxy-3-methylthiopropoxy)-chromone2-carboxylic acid, is filtered and dried; m.p. 200°–202° C.

The percentages of inhibition, in comparison with the controls, of the allergic reaction induced by passive cutaneous anaphylaxis in rats treated with 0.1 ml of an homologous antiserum diluted 1/10 and injected by intradermal route, are summarized in table I.

TABLE I

| Product | Dose (mg/kg) os | Δ % in comparison with controls | LD$_{50}$ mouse (mg/kg) os |
|---|---|---|---|
| CM 57201 (Ex. 1) | 10 100 | −65.55°° −75.12°° | >1000 |
| CM 57249 (Ex. 2) | 50 100 | −73.00°° −75.77°° | >1000 |
| CM 57251 (Ex. 3) | 100 | −69.12°° | >1000 |
| CM 57215 (Ex. 4) | 100 | −75.00°° | >1000 |
| CM 57193 (Ex. 5) | 50 100 | −47.56°° −70.84°° | >1000 |
| CM 57194 (Ex. 6) | 100 | −55.37°° | >1000 |
| product A | 100 | −66.19°° | ≅1000 |
| product B | 100 | −29.17° | ≅1000 |

°significant P ≦ 0.05
°°significant P ≦ 0.01

It results from this table that the representative products of the present invention, even at very low doses, have a remarkable inhibiting power, generally higher than that of the reference compounds A and B.

Table II hereinbelow, shows the percentages of inhibition after oral administration of a representative compound of the present invention (CM 57201, product of example 1) in comparison with the Product C of reference, namely the corresponding derivative having, in the 2-hydroxypropoxy chain at the 5 position of the chromone nucleus, a methoxy group instead of a methylthio group.

TABLE II

| Product | Dose (mg/kg) os | Δ % in comparison with controls |
|---|---|---|
| CM 57201 | 10 | −65.55°° |
| product C | 10 | +8.71* |

*non significant
°°significant P ≤ 0.01

It results from the table that the representative compound of the present invention induces an inhibition of the passive cutaneous anaphylaxis at a dose of 10 mg/kg, whereas the reference product is inactive at the same dose.

Table III shows the percentages of inhibition after oral administration of a representative compound of the present invention (CM 57202, product of example 6) in comparison with the Product D of reference, namely its isomer in 7 position of the chromone ring.

TABLE III

| Product | Dose (mg/kg) os | Δ % in comparison with controls |
|---|---|---|
| CM 57202 | 10 | −52.95°° |
|  | 100 | −70.40°° |
| product D | 10 | +17.83* |
|  | 100 | −16.17* |
|  | 200 | −30.07° |

*non significant
°significant P ≤ 0.05
°°significant P ≤ 0.01

It results from this table that the representative product of the present invention induces a significant inhibition of the passive cutaneous anaphylaxis when it is administered at an oral dose of 10 mg/kg, whereas the reference product is almost inactive even at doses 10 times higher.

The ability of the 5-(2-hydroxy-3-thiopropoxy) chromone-2-carboxylic acids of the present invention and of the salts and esters thereof of inhibiting—by oral as well as by intravenous route—the passive cutaneous anaphylaxis in rats sensitized to egg albumin and *Bordetella pertussis* has been compared to that of two reference compounds:

product E: 1,3-bis-(2-carboxy-5-chromonyloxy)propane-2-ol sodium salt, well known by its international nonproprietary name "sodium chromoglycate";

product F: 5-(2-hydroxy-3-p-cyanophenoxypropoxy)chromone-2-carboxylic acid described in the U.S. Pat. No. 3,953,604.

Table IV shows the $ED_{50}$ of two representative compounds of the present invention (CM 57201, product of example 1 and CM 57202, product of example 6), in comparison with the reference compounds E and F.

TABLE IV

| Product | $ED_{50}$ (mg/kg) os | i.v. |
|---|---|---|
| CM 57201 | 5.39 | 0.11 |
| CM 57202 | 38.11 | 0.13 |
| Product E | inactive | 1.15 |
| Product F | inactive | 0.29 |

It results from this table that the products of the present invention, contrary to the reference products, are active by oral route and that their activity by intravenous route is about 3 times higher than that of the product F and 10 times higher than that of sodium cromoglycate.

Due to their anti-anaphylactic and anti-allergic activity, the 5-(2-hydroxy-3-thiopropoxy)chromones of the present invention can be useful for the treatment, for example, of allergic asthma, hay fever, and generally of conditions due mainly to the combination of a specific antigen with a reaginic antibody.

As medicaments, the products of the present invention can be administered orally, parenterally or by inhalation, either alone or as appropriate pharmaceutical preparations, such as tablets, powder, granules, capsules, elixirs, suspensions, syrups and as solutions or suspensions for injection or inhalation.

Pharmaceutical preparations for oral administration include, in addition to the active substance, one or more organic or mineral carriers which will be pharmaceutically acceptable and compatible with the active ingredient, as well as sweetening agents, flavoring agents, coloring agents, preserving agents and the like.

Tablets can be prepared by utilising, as carriers, inert diluents such as calcium carbonate, sodium carbonate, lactose, talc, granulating and disintegrating agents, such as starch and alginic acid, binding agents such as starch, gelatine and acacia, lubricating agents such as magnesium stearate and stearic acid. The tablets can be coated or not. The coating is made with the purpose of delaying the decomposition and the absorption of the active substance in the gastro-intestinal tract, thus giving a long lasting effect.

Suspensions, syrups and elixirs may contain, in addition to the active substance, suspending agents such as methylcellulose, tragacanth, sodium alginate and the like, wetting agents such as lecithin, polyoxyethylene stearate, polyoxyethylene sorbitan monooleate and preservatives such as ethyl p-hydroxybenzoate. Capsules may contain the active substance either alone or in admixture with inert solid diluents such as, for example, calcium carbonate, calcium phosphate and kaolin.

For administration by inhalation, the compositions according to the invention can be in the form of a powder or aerosol spray.

The compositions above can also include other active ingredients such as, for example, bronchodilators, antitussives, antihistamines or tranquillizing agents.

The 5-(2-hydroxy-3-thiopropoxy)chromone-2-carboxylic acids, as well as their salts and their $C_1$-$C_4$ alkyl esters can be administered by oral route at variable dosages of from 5 to 1000 mg or by inhalation at a dosage of 0.5–15 mg. They are preferably administered in the pharmaceutical compositions of the present invention in dosage unit form comprising from 5 to 250 mg of active ingredient in admixture with a pharmaceutical carrier as specified above.

The following examples illustrate the invention without limiting it. In the examples, as well as in the specification and in the claims, the products are defined "chromone-2-carboxylic acids". It is understood that the nomenclature of the products of the present invention reads as follows:

5-(2-hydroxy-3-hydroxypropoxy)-4-oxo-4H-chromene-2-carboxylic acids and that the term "chromone", used for the sake of brevity, designate the "4-oxo-4H-chromene".

PREPARATION

To a cold solution of 5.2 g of sodium hydroxide and 6.3 g of methylmercaptan in 70 ml of water there is added a solution of 24.5. g of 2-hydroxy-6-(3-chloro-2-hydroxypropoxy) acetophenone and 0.2 g of hexadecyltributylphosphonium bromide in 240 ml of toluene. The mixture is left to stand under stirring at 25° C. for 2 hours, then it is acidified with N hydrochloric acid. The toluene is separated, the aqueous layer is extracted with 30 ml of toluene, the organic phase is washed with water, dried on sodium sulfate and evaporated to dryness. The residue is taken up with 30 ml of diisopropyl ether and cooled. After filtration and purification 24 g of 2-hydroxy-6-(2-hydroxy-3-methylthiopropoxy)acetophenone is obtained; m.p. 63°–65° C.

In the same manner, by reacting the 2-hydroxy-6-(3-chloro-2-hydroxypropoxy)acetophenone with ethylmercaptan, propylmercaptan, isopropylmercaptan, butylmercaptan and hexylmercaptan respectively, the 2-hydroxy-6-(2-hydroxy-3-ethylthiopropoxy)acetophenone; the 2-hydroxy-6-(2-hydroxy-3-propylthiopropoxy)acetophenone; the 2-hydroxy-6-(2-hydroxy-3-isopropylthiopropoxy)acetophenone; the 2-hydroxy-6-(2-hydroxy-3-butylthiopropoxy)acetophenone and the 2-hydroxy-6-(2-hydroxy-3-hexylthiopropoxy)acetophenone, respectively, are obtained.

EXAMPLE 1

To a solution of 3.3 g of sodium in 80 ml of anhydrous ethanol and 80 ml of anhydrous benzene there is added a mixture of 15.7 g of 2-hydroxy-6-(2-hydroxy-3-methylthiopropoxy)acetophenone, 28.5 g of diethyl oxalate and 40 ml of benzene. The reaction mixture is heated at reflux for 5 hours under stirring, cooled at 20°–30° C. and acidified with hydrochloric acid in ethanol. After heating at reflux for 15 minutes, the mixture is cooled, the clear solution is evaporated to dryness, the residue is washed with hexane, then dissolved in 150 ml of ethyl acetate. The solution thus obtained is washed with water and its volume is reduced to 20–25 ml by evaporation. After purifying on a column of alumina, the solvent is evaporated off and an oil, which cristallizes slowly, is obtained. The product is taken up with diisopropyl ether and filtered. The crude product thus obtained is crystallized from a mixture of 15 ml of ethyl acetate and 40 ml of diisopropyl ether to give 9 g of ethyl 5-(2-hydroxy-3-methylthiopropoxy)chromone-2-carboxylate (CM 57201); m.p. 69°–71° C.

EXAMPLES 2 to 5

According to the procedure set forth in Example 1, by reacting the acetophenones described in the PREPARATION with diethyl oxalate and acidifying with hydrochloric acid, the esters given in table V hereinbelow are obtained.

TABLE V

| EXAMPLES | PRODUCTS |
|---|---|
| 2 | Ethyl 5-(2-hydroxy-3-ethylthiopropoxy)chromone-2-carboxylate (CM 57249); m.p. 66–68° C. (crystallized from diisopropyl ether). |
| 3 | Ethyl 5-(2-hydroxy-3-propylthiopropoxy)chromone-2-carboxylate (CM 57251); m.p. 63–66° C. (crystallized from diisopropyl ether). |
| 4 | Ethyl 5-(2-hydroxy-3-isopropylthiopropoxy)chromone-2-carboxylate (CM 57215); m.p. 66–69° C. (crystallized from diisopropyl ether). |
| 5 | Ethyl 5-(2-hydroxy-3-butylthiopropoxy)chromone-2-carboxylate (CM 57193); m.p. 50–52° C. (crystallized from diisopropyl ether). |

EXAMPLE 6

To a solution of 3.4 g of ethyl 5-(2-hydroxy-3-methylthiopropoxy)chromone-2-carboxylate in 20 ml of acetone there is added 11 ml of N sodium hydroxide and the mixture is heated at 50° C. for 10 minutes. After evaporating the solvent under reduced pressure, 30 ml of water are added, the resulting mixture is extracted with diethyl ether, filtered on charcoal and the limpid solution thus obtained is acidified with hydrochloric acid. The product which precipitates is filtered, washed with water and dried. Thus, 2.8 g of 5-(2-hydroxy-3-methylthiopropoxy)chromone-2-carboxylic acid is obtained as dihydrate (CM 57202); m.p. 76°–79° C.

In the same manner, by hydrolysing the ethyl 5-(2-hydroxy-3-butylthiopropoxy)chromone-2-carboxylate, the 5-(2-hydroxy-3-butylthiopropoxy)chromone-2-carboxylic acid monohydrate (CM 57194) is obtained; m.p. 58°–61° C.

EXAMPLE 7

A mixture of 3.7 g of 5-(2-hydroxy-3-butylthiopropoxy)chromone-2-carboxylic acid monohydrate and 10 ml of N sodium hydroxide is stirred for 10 minutes and the precipitate which forms is filtered, washed with a little acetone and dried. Thus, 3.5 g sodium 5-(2-hydroxy-3-butylthiopropoxy)chromone-2-carboxylate is obtained.

EXAMPLE 8

To a solution of 2.7 g of sodium in 60 ml of anhydrous ethanol and 60 ml of anhydrous benzene there is added a mixture of 15.2 g of 2-hydroxy-6-(2-hydroxy-3-hexylthiopropoxy)acetophenone, 21 g of diethyl oxalate and 30 ml of benzene. The reaction mixture is heated at reflux under stirring for 5 hours, then it is cooled to 20°–30° C. and acidified with hydrochloric acid in ethanol. After heating at reflux for 15 minutes, the mixture is cooled, the clear solution is evaporated to dryness, the residue is washed with hexane then dissolved in 150 ml of ethyl acetate. The solution thus obtained is washed with water and its volume reduced to 20–25 ml by evaporation. After purifying on a column of alumina, the solvent is evaporated off and an oil is obtained which is dissolved in 80 ml of acetone and 36 ml of N sodium hydroxide. The solution thus obtained is heated for 10 minutes, then cooled and the precipitate which forms is filtered, washed with a water-acetone mixture and dissolved in 500 ml of hot water. The mixture is acidified with hydrochloric acid, the precipitate is filtered, washed with water and dried. Thus, 10 g of 5-(2-hydroxy-3-hexylthiopropoxy)chromone-2-carboxylic acid (CM 57209) are obtained; m.p. 97°–100° C.

EXAMPLES 9 and 10

According to the procedure set forth in Example 1, by reacting the 2-hydroxy-6-(2-hydroxy-3-methylthiopropoxy)acetophenone with diisopropyl or n-butyl oxalate and acidifying with hydrochloric acid, the esters given in table VI hereinbelow are obtained.

TABLE VI

| EX. | PRODUCTS |
|---|---|
| 9 | Isopropyl 5-(2-hydroxy-3-methylthiopropoxy)chromone-2-carboxylate (CM 57524); m.p. 71–73° C. (crystallized from diisopropyl ether), |
| 10 | n-butyl 5-(2-hydroxy-3-methylthiopropoxy)chromone- |

TABLE VI-continued

| EX. | PRODUCTS |
|---|---|
| | 2-carboxylate (CM 57525); yellow oil |

$n_D^{20}$ = 1,5648; the resulting yellow oil crystallizes spontaneously after a few days and then melts at 52–54° C.

We claim:

1. A compound selected from the group consisting of 5-(2-hydroxy-3-thiopropoxy)chromone-2-carboxylic acids of the formula

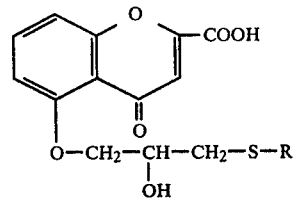

wherein R is a member selected from the group consisting of alkyl groups of from 1 to 16 carbon atoms, alkenyl groups of 3 to 4 carbon atoms, cycloalkyl groups of from 3 to 8 carbon atoms and cycloalkylalkyl groups of from 4 to 9 carbon atoms; and alkali and alkaline-earth metal salts thereof; and alkyl esters thereof having 1 to 4 carbon atoms.

2. A compound selected from the group consisting of the 5-(2-hydroxy-3-methylthiopropoxy)chromone-2-carboxylic acid and the alkali and alkaline-earth metal salts thereof and the alkyl esters thereof having from 1 to 4 carbon atoms.

3. Ethyl 5-(2-hydroxy-3-methylthiopropoxy)chromone-2-carboxylate.

4. The compound as recited in claim 1, 2, or 3 in admixture with a pharmaceutical carrier wherein said compound is present in the range from 5 to 250 milligrams by weight and serves as an active ingredient to inhibit allergic reactions.

* * * * *